US009500850B2

(12) United States Patent
Fukuda et al.

(10) Patent No.: US 9,500,850 B2
(45) Date of Patent: Nov. 22, 2016

(54) CULTURE MICROSCOPE

(71) Applicant: OLYMPUS CORPORATION, Shibuya-ku, Tokyo (JP)

(72) Inventors: Tatsushi Fukuda, Tokyo (JP); Hiroyasu Hebiishi, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 14/639,614

(22) Filed: Mar. 5, 2015

(65) Prior Publication Data
US 2015/0260974 A1 Sep. 17, 2015

(30) Foreign Application Priority Data
Mar. 14, 2014 (JP) ................................ 2014-051885

(51) Int. Cl.
G02B 21/26 (2006.01)
C12M 1/00 (2006.01)
C12M 1/34 (2006.01)

(52) U.S. Cl.
CPC .............. *G02B 21/26* (2013.01); *C12M 41/14* (2013.01); *C12M 41/36* (2013.01)

(58) Field of Classification Search
CPC ...... G02B 21/26; C12M 41/14; C12M 41/36
USPC ......................................................... 359/391
See application file for complete search history.

(56) References Cited

U.S. PATENT DOCUMENTS

| | | | | |
|---|---|---|---|---|
| 6,980,293 | B1 * | 12/2005 | Harada | G01N 21/6458 356/246 |
| 7,233,438 | B2 * | 6/2007 | Tokunaga | B01L 7/00 250/310 |
| 2004/0051051 | A1 * | 3/2004 | Kato | G01N 21/6402 250/458.1 |
| 2004/0241832 | A1 * | 12/2004 | Muraki | C12M 41/46 435/287.1 |
| 2005/0248836 | A1 * | 11/2005 | Tsuchiya | G01N 21/0332 359/368 |
| 2005/0282268 | A1 * | 12/2005 | Kagayama | C12M 23/50 435/288.7 |
| 2006/0092506 | A1 * | 5/2006 | Tsuchiya | G02B 7/008 359/395 |
| 2006/0141613 | A1 * | 6/2006 | Tsuchiya | C12M 41/14 435/288.7 |

(Continued)

FOREIGN PATENT DOCUMENTS

| | | |
|---|---|---|
| EP | 1677136 A1 | 7/2006 |
| JP | 2006308746 A | 11/2006 |

OTHER PUBLICATIONS

Extended European Search Report dated Aug. 11, 2015, issued in counterpart European Application No. 15157558.6.

*Primary Examiner* — Frank Font
(74) *Attorney, Agent, or Firm* — Holtz, Holtz & Volek PC

(57) ABSTRACT

Provided is a culture microscope including a culturing space that is provided with a stage on which a specimen is mounted; an adjacent space that is adjacent to the culturing space and in which a driving mechanism of the stage is disposed; a stationary partition that divides the adjacent space and the culturing space and that is also provided with a first through-hole; a tabular movable partition that is disposed at a position where the movable partition closes the first through-hole, that has a second through-hole that is smaller than the first through-hole, that is supported so as to be movable parallel to the stationary partition, and that is larger than the first through-hole; and a lid member that is disposed at a position where the lid member closes the second through-hole of the movable partition and that is supported so as to be movable parallel to the movable partition.

9 Claims, 4 Drawing Sheets

(56) References Cited

U.S. PATENT DOCUMENTS

| | | | |
|---|---|---|---|
| 2006/0194193 A1* | 8/2006 | Tsuruta | C12M 29/10 435/4 |
| 2008/0247038 A1* | 10/2008 | Sasaki | G02B 21/0024 359/395 |
| 2008/0266653 A1* | 10/2008 | Korpinen | G02B 21/26 359/368 |
| 2009/0021111 A1* | 1/2009 | Ue | G02B 21/26 310/317 |
| 2011/0091964 A1* | 4/2011 | Tateyama | G06T 1/0014 435/287.1 |
| 2011/0091965 A1* | 4/2011 | Tateyama | G06T 1/0014 435/287.1 |
| 2011/0134516 A1* | 6/2011 | Araya | G02B 21/0004 359/371 |
| 2011/0164316 A1* | 7/2011 | Kassen | G02B 21/26 359/391 |
| 2014/0233097 A1* | 8/2014 | Ue | G02B 21/26 359/391 |
| 2014/0295535 A1* | 10/2014 | Kitahara | G01N 21/6458 435/288.7 |
| 2015/0143940 A1* | 5/2015 | Choi | G02B 21/26 74/480 R |

* cited by examiner

CULTURE MICROSCOPE

TECHNICAL FIELD

This application is based on Japanese Patent Application No. 2014-051885, the contents of which are incorporated herein by reference.

The present invention relates to a culture microscope.

BACKGROUND ART

In the related art, there is a known culture microscope that is provided with an adjacent space that is divided by a partition in a nearly airtight state at a portion below a culturing space for culturing specimens and that is provided with, in this adjacent space, a moving mechanism, electrical components, and so forth for moving the specimens in the culturing space (for example, see Patent Literature 1).

CITATION LIST

Patent Literature

{PTL 1} Japanese Unexamined Patent Application, Publication No. 2006-308746

SUMMARY OF INVENTION

Technical Problem

However, in the culture microscope of Patent Literature 1, it is not possible to provide a large opening in the partition that divides the culturing space and the adjacent space due to the necessity to divide the two spaces in a nearly airtight state, and there is a disadvantage in that the stroke of the moving mechanism that moves the specimens is restricted.

The present invention has been conceived in light of the above-described circumstances, and an object thereof is to provide a culture microscope with which it is possible to achieve a sufficient stroke for observing a specimen while ensuring a nearly-airtight divided state between a culturing space and a bottom space, and with which it is possible to observe numerous specimens while culturing them.

Solution to Problem

In order to achieve the above-described object, the present invention provides the following solutions.

An aspect of the present invention provides a culture microscope including a culturing space that is provided with a stage on which a specimen is mounted and in which the specimen is cultured; an adjacent space that is disposed adjacent to the culturing space and in which a driving mechanism that drives the stage is disposed; a stationary partition that divides the adjacent space and the culturing space and that is provided with a first through-hole that passes through the stationary partition in a thickness direction; a tabular movable partition that is disposed at a position where the movable partition closes the first through-hole of the stationary partition, that has a second through-hole that is smaller than the first through-hole, that is supported so as to be movable parallel to the stationary partition, and that is larger than the first through-hole; and a lid member that is disposed at a position where the lid member closes the second through-hole of the movable partition and that is supported so as to be movable parallel to the movable partition, wherein the driving mechanism is connected to the lid member via a shaft that passes through the first through-hole and the second through-hole, and the stage is secured to the lid member.

With this aspect, because the first through-hole provided in the stationary partition that divides the culturing space and the adjacent space is closed by the movable partition, and the second through-hole provided in the movable partition is closed by the lid member, the culturing space and the adjacent space are sufficiently divided despite the presence of the first through-hole. When a specimen is mounted on the stage in the culturing space, and the driving mechanism is operated in the adjacent space, the shaft that connects the driving mechanism and the lid member moves the lid member while moving in the second through-hole in the direction parallel to the partition.

In addition, when the shaft is moved further, by moving the movable partition with respect to the stationary partition, it becomes possible to move the shaft within the area of the first through-hole, which is larger than the second through-hole. In this case, because the first through-hole of the stationary partition is closed by the movable partition, and the second through-hole of the movable partition is closed by the lid member, the first through-hole is maintained in the closed state even if the lid member that is connected to the shaft is moved within the area of the first through-hole.

Specifically, while maintaining the closed state of the first through-hole provided in the stationary partition, it is possible to move the stage, which is secured to the lid member in the culturing space, within the area of the first through-hole by means of the driving mechanism provided in the adjacent space, and thus, it is possible to ensure a sufficient stroke for moving the specimen.

In the above-described aspect, a cylindrical first protrusion that protrudes toward the movable partition and whose tip comes into contact with a surface of the movable partition in a movable manner may be provided at a periphery of the first through-hole of the stationary partition over the entire circumference thereof; and a first engaging protrusion that protrudes toward the stationary partition and that can be engaged with the first protrusion may be provided at an outer periphery of the movable partition.

By doing so, when the movable partition is moved due to the movement of the shaft, the movable partition can be moved until the first engaging protrusion provided at the outer periphery of the movable partition engages with the first protrusion provided at the periphery of the first through-hole, and, during this movement, contact between the surface of the movable partition and the tip of the first protrusion is maintained. Accordingly, it is possible to achieve an airtight state between the movable partition and the stationary partition.

In addition, in the above-described aspect, a first seal member that forms a seal between the tip of the first protrusion and a surface of the movable partition over the entire circumference thereof may be provided.

By doing so, because a gap between the movable partition and the stationary partition is sealed over the entire circumference thereof by the first seal member, it is possible to prevent the atmosphere inside the culturing container from leaking into the adjacent space.

In addition, in the above-described aspect, a cylindrical second protrusion that protrudes toward the lid member and whose tip comes into contact with a surface of the lid member in a movable manner may be provided at a periphery of the second through-hole of the movable partition over the entire circumference thereof; and a second engaging protrusion that protrudes toward the movable partition and that can be engaged with the second protrusion may be provided at an outer periphery of the lid member.

By doing so, when the lid member is moved due to the movement of the shaft, the lid member can be moved until the second engaging protrusion provided at the outer periphery of the lid member engages with the second protrusion provided at the periphery of the second through-hole, and, during this movement, contact between the surface of the lid member and the tip of the second protrusion is maintained. Accordingly, it is possible to achieve an airtight state between the lid member and the movable partition.

In addition, in the above-described aspect a second seal member that forms a seal between the tip of the second protrusion and a surface of the lid member over the entire circumference thereof may be provided.

By doing so, because a gap between the lid member and the movable partition is sealed over the entire circumference thereof by the second seal member, it is possible to prevent the atmosphere inside the culturing container from leaking into the adjacent space.

In addition, in the above-described aspect, the movable partition may be formed by stacking, in the thickness direction, a plurality of tabular plates having the second through-holes of different sizes, and the plates may be disposed so as to allow relative movement with respect to each other in directions parallel to surfaces thereof.

By doing so, it is possible to ensure a large amount of movement for the shaft even if the amounts of movement for the individual plates are reduced, and it is possible to achieve a compact configuration by reducing the dimensions of the plates.

In addition, in the above-described aspect, a cylindrical third protrusion that protrudes toward another one of the plates and whose tip comes into contact with a surface of the other one of the plates in a movable manner may be provided at a periphery of the second through-hole of one of the plates over the entire circumference thereof; and an engaging protrusion that protrudes toward the one of the plates and that can be engaged with the third protrusion may be provided at an outer periphery of the other one of the plates.

By doing so, when the shaft is moved in the second through-hole, thereby moving the other one of the plates, because the engaging protrusion provided in the other one of the plates engages with the third protrusion provided in the one of the plates and moves the one of the plates in a dragging manner, it is possible to increase the moving area of the shaft by moving the second through-hole. Accordingly, it is possible to ensure a large amount of movement for the shaft by reducing the amounts of movement for the individual plates.

In addition, in the above-described aspect, a third seal member that forms a seal between the tip of the third protrusion and a surface of the other one of the plates over the entire circumference thereof may be provided.

By doing so, a gap between plates that are moved with respect to each other is sealed by the third seal member, which makes it possible to divide the culturing space and the adjacent space in an airtight state.

In addition, in the above-described aspect, the adjacent space may be provided below the culturing space, and the movable partition may be provided above the stationary partition.

By doing so, because the weight of the movable partition acts on the stationary partition, it is possible to enhance the sealing performance by enhancing the state of contact between the two partitions by means of gravity.

Advantageous Effects of Invention

The present invention affords advantages in that it is possible to achieve a sufficient stroke for moving a specimen while ensuring an airtight state between a culturing space and a bottom space, and it is possible to observe numerous specimens while culturing them.

DESCRIPTION OF EMBODIMENT

A culture microscope 1 according to an embodiment of the present invention will be described below with reference to the drawings.

Figure 1:
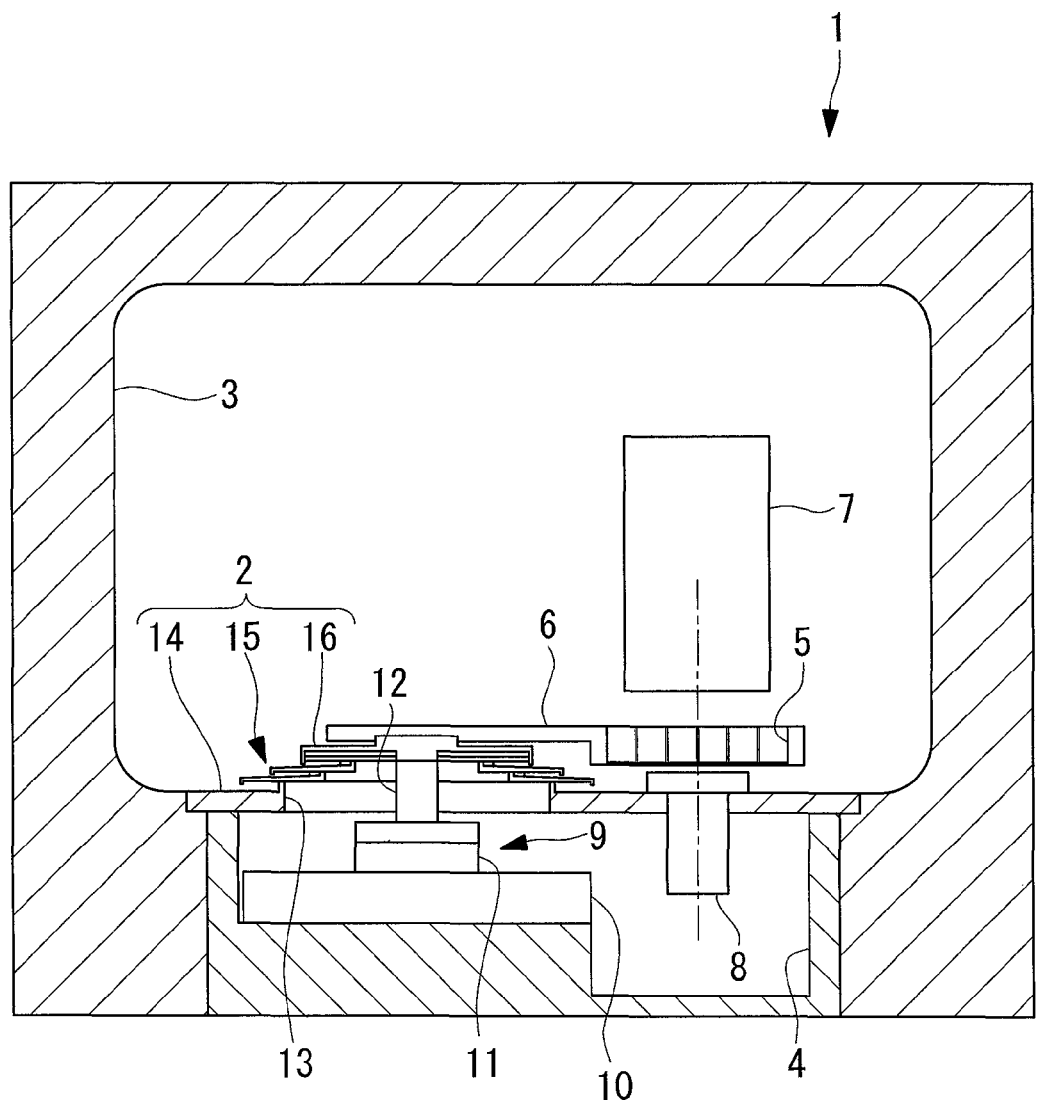
FIG. 1 is a cross-sectional view showing a culture microscope according to an embodiment of the present invention.

As shown in FIG. 1, the culture microscope 1 according to this embodiment is provided with a culturing space 3 and a bottom space 4 that are divided in the vertical direction by a partitioning wall 2.

The culturing space 3 is a space for culturing specimens, that is, observation subjects such as cells or the like, and is configured so as to maintain a suitable environment for culturing, such as, among others, a temperature of 37° C., a humidity of 95%, and, for example, a $CO_2$ concentration of 5% in a low-oxygen state. In the culturing space 3, a stage 6 on which a culturing container 5 that accommodates numerous specimens is mounted and an illumination optical system 7 that radiates illumination light onto the specimens mounted on the stage 6 are disposed. The stage 6 is supported so as to be horizontally movable in two axial directions and is configured so that specimens at individual positions in the culturing container 5 can be placed on the optical axis of the illumination optical system 7 by moving the culturing container 5 mounted on the stage 6 in horizontal directions.

As shown in FIG. 1, in the bottom space 4, on the other hand, an observation optical system 8 that is disposed vertically below the illumination optical system 7, with the stage 6 interposed therebetween, and a driving mechanism 9 that drives the stage 6 are disposed. The driving mechanism 9 is provided with a pair of linear motion mechanisms 10 and 11 that are arranged orthogonal to each other and is configured so that a shaft 12 connected to the stage 6 can be horizontally moved in the two axial directions.

The partitioning wall 2 that divides the culturing space 3 and the bottom space 4 in the vertical direction is provided with a horizontal tabular stationary partition 14 that has a through-hole (first through-hole) 13 that passes therethrough in the vertical direction (thickness direction), a movable partition 15 that is supported so as to be movable in the horizontal direction with respect to the stationary partition 14, and a lid member 16 that is supported so as to be movable in the horizontal direction with respect to the movable partition 15.

Figure 2:
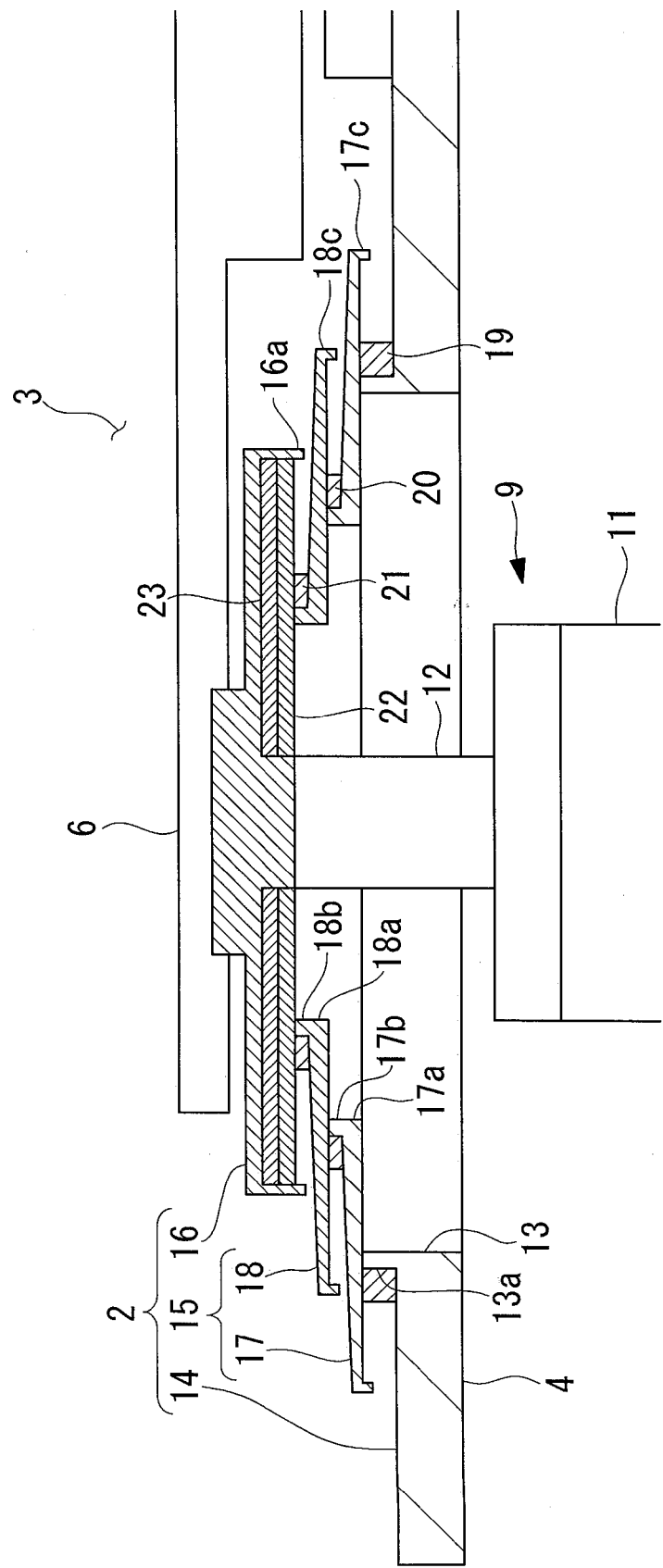
FIG. 2 is an enlarged cross-sectional view showing a partition portion of the culture microscope in FIG. 1

As shown in FIG. 2, in this embodiment, the movable partition 15 is provided with two plates 17 and 18. The first plate 17 is disposed at a position where the first plate 17 closes the through-hole 13 of the stationary partition 14 and the size thereof is such that the first plate 17 extends outward in the horizontal direction farther than the through-hole 13 in a flange-like manner. In addition, the first plate 17 is provided with a through-hole (second through-hole) 17a that is smaller than the through-hole 13 of the stationary partition 14.

The second plate 18 is disposed at a position where the second plate 18 closes the through-hole 17a of the first plate 17 and the size thereof is such that the second plate 18 extends outward in the horizontal direction farther than the through-hole 17a of the first plate 17 in a flange-like manner. In addition, the second plate 18 is provided with a through-hole (third through-hole) 18a that is smaller than the through-hole 17a of the first plate 17.

The two plates 17 and 18 are stacked in the thickness direction and are supported so as to allow relative movement in the horizontal direction with respect to each other.

The lid member 16 is disposed at a position where the lid member 16 closes the through-hole 18a of the second plate 18 and the size thereof is such that the lid member 16 extends outward in the horizontal direction farther than the through-hole 18a of the second plate 18 in a flange-like manner. The lid member 16 is not provided with a through-hole, and is configured so as to close the through-hole 18a of the second plate 18. In addition, the shaft 12 of the driving mechanism 9 disposed in the bottom space 4 is secured to a bottom surface of the lid member 16. Furthermore, the stage 6 on which the culturing container 5 is mounted is secured to a top surface of the lid member 16.

At peripheries of the through-holes 13 of the stationary partition 14 and those of the through-holes 17a and 18a of the individual plates 17 and 18 of the movable partition 15, cylindrical protrusions 13a, 17b, and 18b that extend upward over the entire circumferences thereof are provided. On the other hand, at the outer peripheries of the individual plates 17 and 18 of the lid member 16 and the movable partition 15, engaging protrusions 16a, 17c, and 18c that extend downward over the entire circumferences thereof are provided.

At the periphery of the protrusion 13a provided in the stationary partition 14, a seal member 19 that comes in contact with a bottom surface of the first plate 17 in a tight-contact state is provided over the entire circumference thereof. In addition, at the periphery of the protrusion 17b provided in the first plate 17, a seal member 20 that comes in contact with a bottom surface of the second plate 18 in a tight-contact state is provided over the entire circumference thereof. Furthermore, at the periphery of the protrusion 18b provided in the second plate 18, a seal member 21 that comes in contact with a bottom surface of the lid member 16 in a tight-contact state is provided over the entire circumference thereof.

The individual seal members 19, 20, and 21 are configured so as to seal gaps formed between their counterparts and themselves, while supporting the counterparts that come into contact with them so as to allow relative movement thereof. Note that it is permissible to provide top-end surfaces of the protrusions 13a, 17b, and 18b with a sealing function instead of separately providing the seal members 19, 20, and 21.

The operation of the thus-configured culture microscope 1 according to this embodiment will be described below.

To observe specimens by using the culture microscope 1 according to this embodiment while culturing the specimens, the culturing container 5 accommodating the specimens is mounted on the stage 6 disposed in the culturing space 3, and the interior environment of the culturing space 3 is set to a temperature of 37° C., a humidity of 95%, and, for example, a $CO_2$ concentration of 5% in a low-oxygen state, namely, to an environment suitable for culturing.

In this state, because cells that serve as the specimens grow, the illumination light is radiated onto the specimens from the illumination optical system 7 periodically or as needed, fluorescence that has been generated at the specimens and that has passed through the bottom surface of the culturing container 3 is collected by the observation optical system 8 that is disposed in the bottom space 4 so as to face upward, and a fluorescence image is acquired, thus allowing the specimens to be observed while culturing them.

In this case, with the culture microscope 1 according to this embodiment, the stage 6 disposed in the culturing space 3 is connected to the driving mechanism 9 in the bottom space 4 via the shaft 12 that passes through the through-hole 13 provided in the stationary partition 14, and it is possible to horizontally move the specimens mounted thereon in the two axial directions via the operation of the driving mechanism 9.

The through-hole 13 of the stationary partition 14 is sealed by bringing the first plate 17 and the seal member 19 into contact with each other; the through-hole 17a of the first plate 17 is sealed by bringing the second plate 18 and the seal member 20 into contact with each other; and the through-hole 18a of the second plate 18 is sealed by bringing the lid member 16 and the seal member 21 into contact with each other. Accordingly, the culturing space 3 and the bottom space 4 are sealed in an airtight state, and, in particular, high humidity gas (in particular, gas such as $CO_2$) in the culturing space 3 is prevented from flowing into the bottom space 4.

Therefore, it is possible to keep the humidity in the bottom space 4 sufficiently low, and thus, it is possible to prevent rusting of mechanical components and electrical components of the driving mechanism 9 or the like. In addition, it is possible to minimize leakage of gas such as $CO_2$, and thus, it is possible to maintain the culturing space 3 and to avoid wasteful consumption of $CO_2$ gas.

Figure 3A:
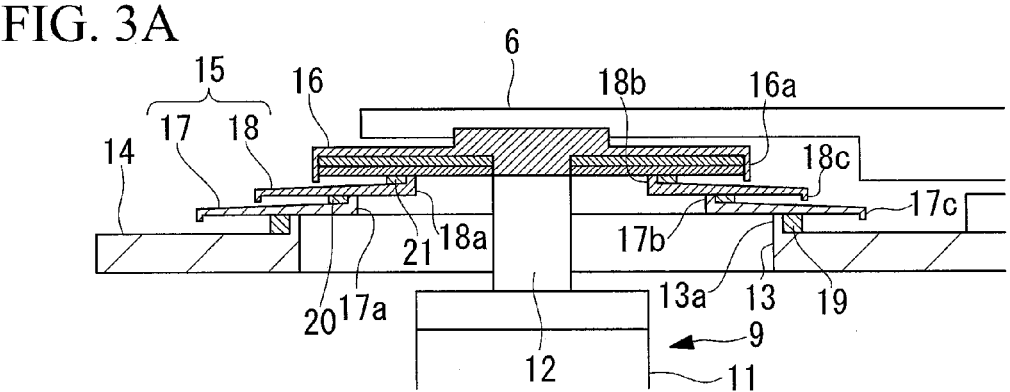
FIG. 3A is a cross-sectional view for explaining the operation of the partition portion of the culture microscope in FIG. 1 and shows a state in which a shaft is disposed at a center of a through-hole.

Also, when the shaft 12 is moved in the horizontal direction from the position shown in FIG. 3A via the operation of the driving mechanism 9, although the lid member 16 secured to the top end of the shaft 12 and the stage 6 secured to the lid member 16 are moved in the horizontal direction, because the bottom surface of the lid member 16 and the seal member 21 are maintained in a tight-contact state even during this movement also, it is possible to continue to divide the culturing space 3 and the bottom space 4 in the airtight state.

Figure 3B:
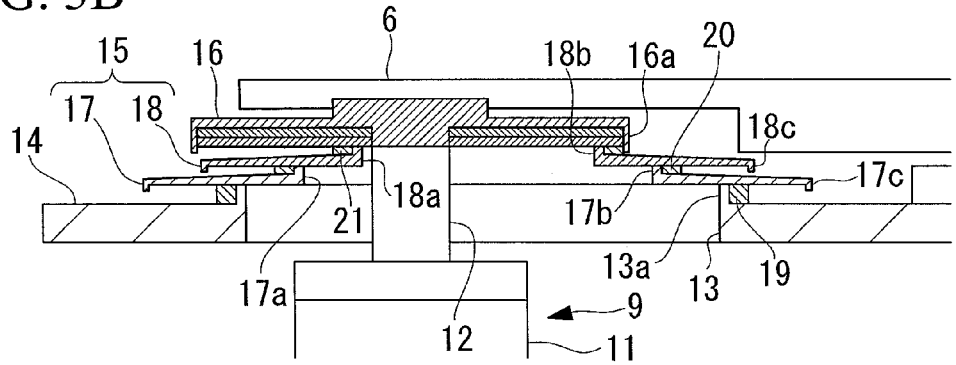
FIG. 3B is a cross-sectional view for explaining the operation of the partition portion of the culture microscope in FIG. 1 and shows a state in which a lid member has been moved together with the shaft.

In addition, as shown in FIG. 3B, when the shaft 12 is moved into close proximity with the inner edge of the through-hole 18a of the second plate 18, the engaging protrusion 16a provided in the lid member 16 engages with the protrusion 18b of the second plate 18 in the horizontal direction. When the shaft 12 continues to be moved further in the same direction from this state, the second plate 18 is also moved in the same direction by being dragged by the lid member 16. Accordingly, the lid member 16 is not removed from the through-hole 18a, thus making it possible to maintain the through-hole 18a of the second plate 18 in the closed state by means of the lid member 16 and also to move the shaft 12 to an area that exceeds the size of the through-hole 18a of the second plate 18.

Figure 3C:
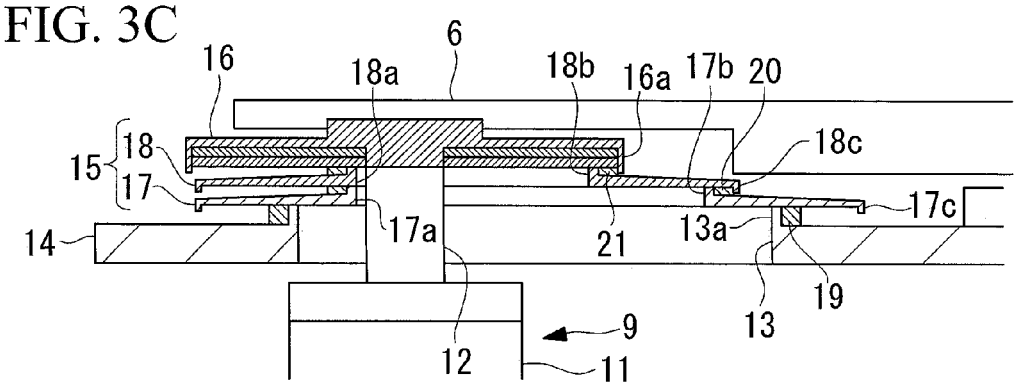
FIG. 3C is a cross-sectional view for explaining the operation of the partition portion of the culture microscope in FIG. 1 and shows a state in which a second plate has been moved together with the shaft.

Furthermore, as shown in FIG. 3C, when the shaft 12 is moved into close proximity with the inner edge of the through-hole 17a of the first plate 17, the engaging protrusion 18c provided in the second plate 18 engages with the protrusion 17b of the first plate 17 in the horizontal direction. When the shaft 12 continues to be moved further in the same direction from this state, the first plate 17 is also moved in the same direction by being dragged by the second plate 18. Accordingly, the second plate 18 is not removed from the through-hole 17a, thus making it possible to maintain the through-hole 17a of the first plate 17 in the closed state by means of the second plate 18 and also to move the shaft 12 to an area that exceeds the size of the through-hole 17a of the first plate 17.

Figure 3D:
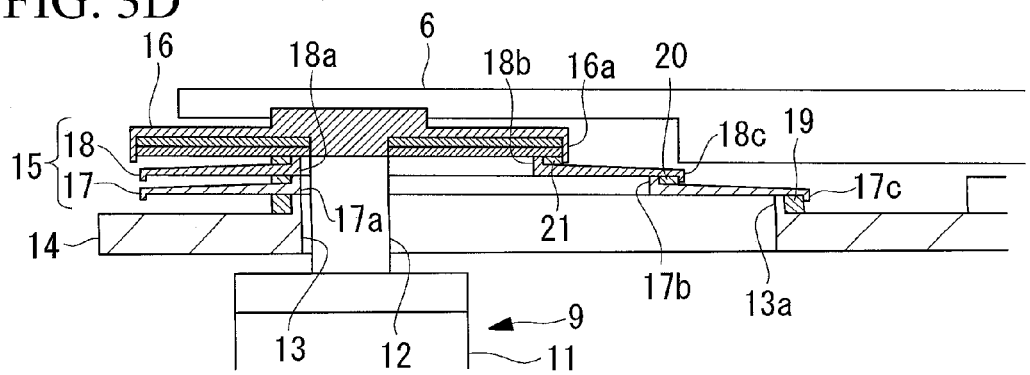
FIG. 3D is a cross-sectional view for explaining the operation of the partition portion of the culture microscope in FIG. 1 and shows a state in which a first plate has moved together with the shaft.

Also, as shown in FIG. 3D, when the shaft 12 is moved into close proximity with the inner edge of the through-hole 13 of the stationary partition 14, the engaging protrusion 17c provided in the first plate 17 engages with the protrusion 13a of the stationary partition 14 in the horizontal direction. Accordingly, the first plate 17 is not removed from the through-hole 13a, thus making it possible to maintain the through-hole 13 of the stationary partition 14 in the closed state by means of the first plate 17.

Figure 4A:
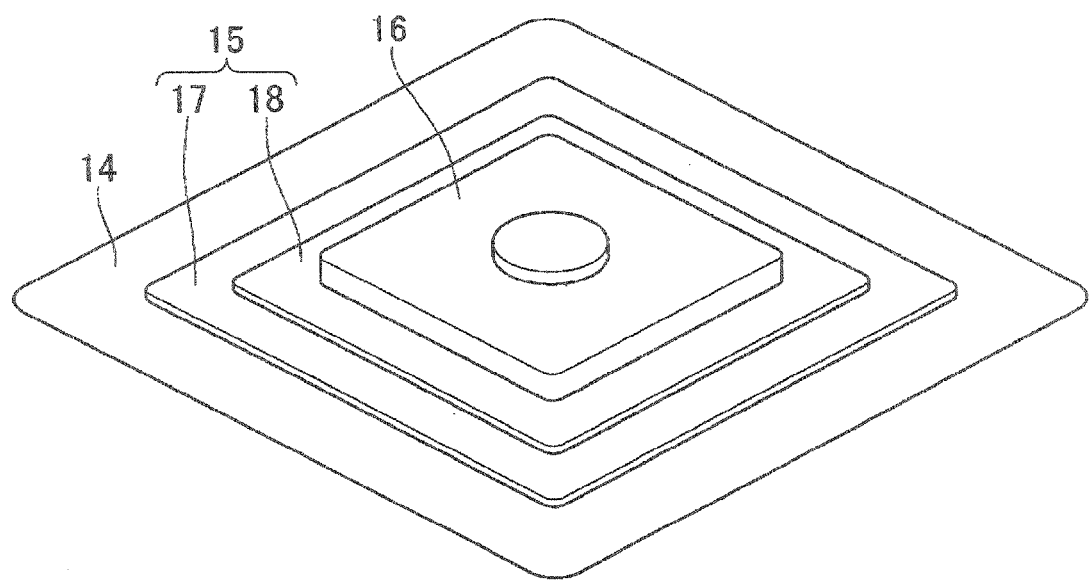
FIG. 4A is a perspective view showing a movable partition and the lid member in the state shown in FIG. 3A.
Figure 4B:
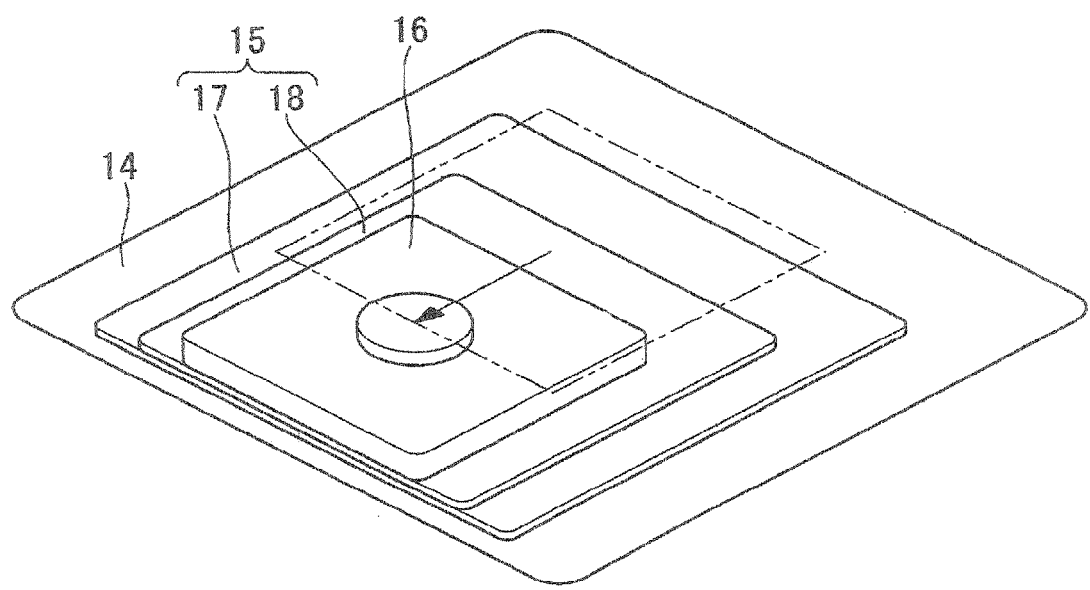
FIG. 4B is a perspective view showing the movable partition and the lid member in the state shown in FIG. 3D.

Specifically, as shown in FIGS. 4A and 4B, with the culture microscope 1 according to this embodiment, there is an advantage in that, by moving the first plate 17 and the second plate 18 so as to follow the movement of the stage 6, it is possible to maintain the through-hole 13 in the airtight state even if the through-hole 13 of the stationary partition 14 is set to be large in order to ensure a large moving area for the stage 6. In FIG. 4B, the chain line indicates the moving area of the center of the lid member 16.

In addition, the two plates 17 and 18 are employed as the movable partition 15 in this embodiment. The number of the plates 17 and 18 is not limited thereto, and it may be one or three or greater. In the case in which the moving area is kept the same, it is possible to reduce the amounts of movement of the individual plates 17 and 18 by increasing the number of plates 17 and 18, and thus, a size reduction is possible by reducing the areas of the plates. In contrast, it is possible to ensure a large moving area for the stage 6 by making the amounts of movement of the individual plates 17 and 18 the same.

In addition, in this embodiment, although the bottom space 4 that is disposed at the portion below the culturing space 3 has been described as an example of the space adjacent to the culturing space 3, it is not limited thereto, and the division may be made in the horizontal direction. However, by dividing the spaces in the vertical direction, there is an advantage in that it is possible to utilize the weight of the constituent components as a biasing force to achieve tight contact of the seal members 19 to 21.

In addition, with the culture microscope 1 according to this embodiment, not only are gaps between the stationary partition 14 and the plate 17, between the plates 17 and 18, and between the plate 18 and the lid member 16 sealed by means of the seal members 19 to 21, but also a simple labyrinth structure is formed by the cylindrical protrusions 13a, 17b, and 18b that are provided in the stationary partition 14 and the plates 17 and 18 and that protrude upward and the cylindrical engaging protrusions 16a, 17c, and 18c that are provided in the lid member 16 and the plates 17 and 18 and that protrude downward. Therefore, if liquid spills in the culturing space 3 for any reason, the spilled liquid can be effectively prevented from flowing into the bottom space 4.

In addition, with the culture microscope 1 according to this embodiment, because the configuration thereof is simple in that the lid member 16 and the two plates 17 and 18 are merely stacked onto the stationary partition 14 from above, there is also an advantage in that the removal thereof is easy and that cleaning is facilitated by this removal when cleaning the culturing space 3.

Note that, in this embodiment, it is permissible to employ a seal member 22 that is fitted to a bottom portion of the lid member 16 so as to be movable in the vertical direction with respect to the lid member 16. In addition, it is permissible to employ a heavy member as the seal member 22; alternatively, it is also permissible to form a member 23 between the lid member 16 and the seal member 22 by using an elastic piece and to utilize the elastic force thereof as a biasing force for achieving tight contact of the seal members 19 to 22.

In addition, a rotation stopper (not shown in the figures) may be provided so that the first plate 17 does not rotate with respect to the stationary partition 14 and so that the second plate 18 does not rotate with respect to the first plate 17.

In addition, although a resin-based material that facilitates sliding is preferable as a material for the seal members 19 to 22, the material may be metal, such as aluminum or the like. In addition, a material containing a lubricant may be used.

REFERENCE SIGNS LIST 1 culture microscope
3 culturing space
4 bottom space (adjacent space)
6 stage
9 driving mechanism
12 shaft
13 through-hole (first through-hole)
13a protrusion (first protrusion)
14 stationary partition
15 movable partition
16 lid member
16a, 17c, 18c engaging protrusion
17, 18 plate
17a through-hole (second through-hole)
17b protrusion (third protrusion)
18b protrusion (second protrusion)
19 seal member (first seal member)
20 seal member (third seal member)
21 seal member (second seal member)

The invention claimed is:
1. A culture microscope comprising:
a culturing space that is provided with a stage on which a specimen is mounted and in which the specimen is cultured;

an adjacent space that is disposed adjacent to the culturing space and in which a driving mechanism that drives the stage is disposed;
a stationary partition that divides the adjacent space and the culturing space and that is provided with a first through-hole that passes through the stationary partition in a thickness direction;
a movable partition that is disposed at a position where the movable partition closes the first through-hole of the stationary partition, wherein the movable partition has a second through-hole that is smaller than the first through-hole, and is supported so as to be movable parallel to the stationary partition, and wherein the movable partition is larger than the first through-hole; and
a lid member that is disposed at a position where the lid member closes the second through-hole of the movable partition and that is supported so as to be movable parallel to the movable partition,
wherein the driving mechanism is connected to the lid member via a shaft that passes through the first through-hole and the second through-hole, and
wherein the stage is secured to the lid member.

2. The culture microscope according to claim 1, wherein:
a cylindrical first protrusion that protrudes toward the movable partition and whose tip comes into contact with a surface of the movable partition in a movable manner is provided at a periphery of the first through-hole of the stationary partition over an entire circumference thereof; and
a first engaging protrusion that protrudes toward the stationary partition and that can be engaged with the first protrusion is provided at an outer periphery of the movable partition.

3. The culture microscope according to claim 2, further comprising a first seal member that forms a seal between the tip of the first protrusion and a surface of the movable partition over an entire circumference thereof.

4. The culture microscope according to claim 1, wherein:
a cylindrical second protrusion that protrudes toward the lid member and whose tip comes into contact with a surface of the lid member in a movable manner is provided at a periphery of a third through-hole of the movable partition over an entire circumference thereof; and
a second engaging protrusion that protrudes toward the movable partition and that can be engaged with the second protrusion is provided at an outer periphery of the lid member.

5. The culture microscope according to claim 4, further comprising a second seal member that forms a seal between the tip of the second protrusion and a surface of the lid member over an entire circumference thereof.

6. The culture microscope according to claim 1, wherein:
the movable partition is formed by stacking, in the thickness direction, a plurality of tabular plates including at least a first plate having the second through-hole, and a second plate having a third through-hole, said second through-hole and said third through-hole having different sizes; and
the plurality of tabular plates are disposed so as to allow relative movement with respect to each other in directions parallel to surfaces thereof.

7. The culture microscope according to claim 6, wherein:
a cylindrical third protrusion is provided at a periphery of the second through-hole over an entire circumference thereof, wherein the third protrusion protrudes toward the second plate, and a tip of the third protrusion comes into contact with a surface of the second plate in a movable manner; and
an engaging protrusion that protrudes toward the first plate and that can be engaged with the third protrusion is provided at an outer periphery of the second plate.

8. The culture microscope according to claim 7, further comprising a third seal member that forms a seal between the tip of the third protrusion and a surface of the second plate over an entire circumference thereof.

9. The culture microscope according to claim 1, wherein the adjacent space is provided below the culturing space, and the movable partition is provided above the stationary partition.

* * * * *